(12) United States Patent
Felding et al.

(10) Patent No.: US 6,743,809 B2
(45) Date of Patent: Jun. 1, 2004

(54) INDOLE DERIVATIVES USEFUL FOR THE TREATMENT OF CNS DISORDERS

(75) Inventors: Jakob Felding, Charlottenlund (DK); Benny Bang-Andersen, Copenhagen (DK); Garrick Paul Smith, Valby (DK); Kim Andersen, Virum (DK)

(73) Assignee: H. Lundbeck A/S, Copenhagen-Valby (DK)

( * ) Notice: Subject to any disclaimer, the term of this patent is extended or adjusted under 35 U.S.C. 154(b) by 0 days.

(21) Appl. No.: 10/347,574

(22) Filed: Jan. 17, 2003

(65) Prior Publication Data

US 2003/0166664 A1 Sep. 4, 2003

Related U.S. Application Data

(63) Continuation of application No. PCT/DK01/00507, filed on Jul. 17, 2001.

(30) Foreign Application Priority Data

Jul. 21, 2000 (DK) ......................................... 2000 01123

(51) Int. Cl.[7] ..................... A61K 31/454; C02D 401/04
(52) U.S. Cl. ..................... 514/323; 546/201; 546/194; 546/256; 546/277.4; 544/129; 544/360; 514/339; 514/333; 514/318; 514/254; 514/235.2
(58) Field of Search ..................... 514/323, 339, 514/333, 318, 254, 235.2; 546/201, 194, 256, 277–4; 544/129, 360

(56) References Cited

U.S. PATENT DOCUMENTS

| 3,980,658 A | 9/1976 | Possanza et al. | 260/293.61 |
| 5,585,374 A | 12/1996 | Cliffe et al. | 514/212 |

FOREIGN PATENT DOCUMENTS

| AT | 332 401 | 1/1976 | C07D/401/02 |
| EP | 0 303 506 | 2/1989 | C07D/401/04 |
| EP | 0 303 507 | 2/1989 | C07D/401/04 |
| WO | 94/24127 | 10/1994 | C07D/403/06 |
| WO | 94/25454 | 11/1994 | C07D/405/12 |
| WO | 96/22290 | 7/1996 | C07D/405/00 |
| WO | 99/11641 | 3/1999 | C07D/401/04 |

OTHER PUBLICATIONS

Michael Rowley, et al., "3–(4–Fluoropiperidin–3–yl)–2–phenylindoles as High Affinity, Selective, and Orally Bioavailable h5–HT$_{2A}$ Receptor Antagonists," *J. Med. Chem.* (2001) 44: 1603–1614.

I. Artaiz et al., "The pharmacology of VA21B7: an atypical 5–HT$_3$ receptor antagonist with anxiolytic–like properties in animal models," *Psychopharmacology* (1995) 117: 137–148.

*Primary Examiner*—Charanjit S. Aulakh
(74) *Attorney, Agent, or Firm*—Darby & Darby

(57) ABSTRACT

The present invention relates to substituted indole derivatives of formula I

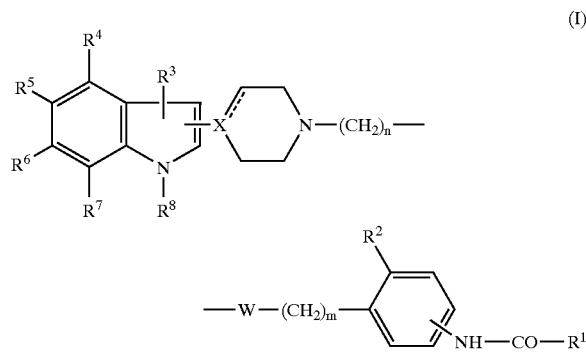

wherein $R^1$ is hydrogen or optionally substituted $C_{1-6}$-alkyl, $C_{2-6}$-alkenyl, $C_{2-6}$-alkynyl, $C_{3-8}$-cycloalkyl or $C_{3-8}$-cycloalkyl-$C_{1-6}$-alkyl, or $R^1$ is optionally substituted aryl, aryl-$C_{1-6}$-alkyl, heteroaryl, heteroaryl-$C_{1-6}$-alkyl or $R^1$ is —NR'R" wherein R' and R" are independently selected from hydrogen and optionally substituted $C_{1-6}$-alkyl, aryl, aryl-$C_{1-6}$-alkyl, heteroaryl and heteroaryl-$C_{1-6}$-alkyl, or $R^1$ is a saturated or partially saturated 5- to 6-membered ring containing one, two or three hetero atoms selected from O or S, and a group N—$R^9$ wherein $R^9$ is hydrogen or optionally substituted $C_{1-6}$-alkyl;

$R^2$ is $C_{1-6}$-alkyl

W, n, X, $R^3$–$R^8$ are as defined in the description.

The compounds of the invention are potent dopamine $D_4$ ligands.

11 Claims, No Drawings

INDOLE DERIVATIVES USEFUL FOR THE TREATMENT OF CNS DISORDERS

This application is a continuation of International application no. PCT/DK01/00507, filed Jul. 17, 2001. The prior application is hereby incorporated by reference in its entirety.

FIELD OF THE INVENTION

The present invention relates to a novel class of indole derivatives having affinity for the dopamine $D_4$ receptor. The compounds have antagonistic effect at the dopamine $D_4$ receptor and are therefore useful in the treatment of certain psychiatric and neurologic disorders, in particular psychoses. Some of the compounds also have affinity for the $5\text{-}HT_{2A}$ and/or the $5\text{-}HT_{2C}$ receptor and some of the compounds are serotonin reuptake inhibitors.

BACKGROUND OF THE INVENTION

AT 332401 discloses compounds of the general formula

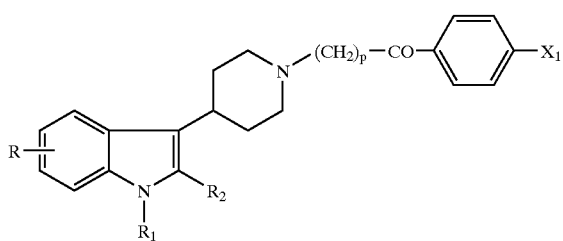

wherein R is hydrogen or alkyl, $R_1$ and $R_2$ are hydrogen or alkyl, p is 2 or 3 and $X_1$ is hydrogen, fluoro, chloro or bromo. The compounds are said to be useful as neuroleptics. The patent does not contain any experimental data.

WO 95/11680 relates to a broad class of compounds having antipsychotic activity. One group of compounds claimed are compounds having the formula

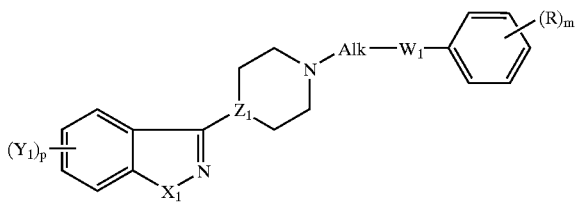

wherein $X_1$ is O, S, NH or $NR_2$, Alk is alkylene, $W_1$ is $CH_2$, O, S or NH, and R is hydrogen, alkyl, alkoxy, hydroxy, carboxyl, halogen, amino, alkylamino, dialkylamino, nitro, alkylthio, trifluoromethoxy, cyano, acylamino, trifluoroacetyl, aminocarbonyl, monoalkylaminocarbonyl, dialkylaminocarbonyl, etc. The application does not explain any mechanism of action, but the compounds are said to have a reduced tendency to cause extrapyramidal side effects.

Dopamine $D_4$ receptors belong to the dopamine $D_2$ subfamily of receptors which is considered to be responsible for the antipsychotic effect of neuroleptics. The side effects of neuroleptic drugs which primarily exert their effect via antagonism of $D_2$ receptors are known to be due to $D_2$ receptor antagonism in the striatal regions of the brain. However, dopamine $D_4$ receptors are primarily located in areas of the brain other than striatum, suggesting that selective antagonists of the dopamine $D_4$ receptor will be devoid of extrapyramidal side effects. This is illustrated by the antipsychotic clozapine, which exerts higher affinity for $D_4$ than $D_2$ receptors and is lacking extrapyramidal side effects (Van Tol et al. Nature 1991, 350, 610; Hadley Medicinal Research Reviews 1996, 16, 507–526, and Sanner Exp. Opin. Ther. Patents 1998, 8, 383–393).

A number of $D_4$ ligands, which were postulated to be selective $D_4$ receptor antagonists (L-745,879 and U-101958), have been shown to possess antipsychotic potential (Mansbach et al. Psychopharmacology 1998, 135, 194–200). However, recently it has been reported that these compounds are partial $D_4$ receptor agonists in various in vitro efficacy assays (Gazi et al. Br. J. Pharmacol. 1998, 124, 889–896 and Gazi et al. Br. J. Pharmacol. 1999, 128, 613–620). Furthermore, it was shown that clozapine, which is an effective antipsychotic, is a silent $D_4$ antagonist (Gazi et al. Br. J. Pharmacol. 1999, 128, 613–620).

Consequently, $D_4$ ligands which are partial $D_4$ receptor agonists or antagonists may have beneficial effects against psychoses.

Dopamine $D_4$ antagonists may also be useful for the treatment of cognitive deficits (Jentsch et al. Psychopharmacology 1999, 142, 78–84).

Furthermore, evidence for a genetic association between the "primarily inattentive" subtype of attention deficit hyperactivity disorder (ADHD) and a tandem duplication polymorphism in the gene encoding the dopamine $D_4$ receptor has been published (McCracken et al. Mol. Psychiatry 2000, 5, 531–536). This clearly indicates a link between the dopamine $D_4$ receptor and ADHD, and ligands affecting this receptor may be useful for the treatment of this particular disorder.

Various effects are known with respect to compounds which are ligands at the different serotonin receptor subtypes. As regards the $5\text{-}HT_{2A}$ receptor, which was previously referred to as the $5\text{-}HT_2$ receptor, the following effects have been reported, e.g.:

Antidepressive effect and improvement of the sleep quality (Meert et al. Drug. Dev. Res. 1989, 18, 119), reduction of the negative symptoms of schizophrenia and of extrapyramidal side effects caused by treatment with classical neuroleptics in schizophrenic patients (Gelders British J. Psychiatry 1989, 155 (suppl. 5), 33). Furthermore, selective $5\text{-}HT_{2A}$ antagonists could be effective in the prophylaxis and treatment of migraine (Scrip Report; "Migraine—Current trends in research and treatment"; PJB Publications Ltd.; May 1991) and in the treatment of anxiety (Colpart et al. Psychopharmacology 1985, 86, 303–305 and Perregaard et al. Current Opinion in Therapeutic Patents 1993, 1, 101–128).

Some clinical studies implicate the $5\text{-}HT_2$ receptor subtype in aggressive behaviour. Furthermore, atypical serotonin-dopamine antagonist neuroleptics have $5\text{-}HT_2$ receptor antagonistic effect in addition to their dopamine blocking properties and have been reported to possess anti-aggressive behaviour (Connor et al. Exp. Opin. Ther. Patents 1998, 8(4), 350–351).

Recently, evidence has also accumulated which support the rationale for selective $5\text{-}HT_{2A}$ antagonists as drugs capable of treating positive symptoms of psychosis (Leysen et al. Current Pharmaceutical Design 1997, 3, 367–390 and Carlsson Current Opinion in CPNS Investigational Drugs 2000, 2(1), 22–24).

Compounds which are 5-HT reuptake inhibitors are well-known antidepressant drugs.

$5\text{-}HT_{2C}$ ligands have been found to augment the effect of 5-HT reuptake inhibitors in microdialysis experiments and animal models, and compounds having 5-HT reuptake inhibiting effect combined with affinity for the 5-HT$_{2C}$ receptor may therefore be particularly useful for the treatment of depression and other disorders responsive to serotonin reuptake inhibitors (PCT application No. PCT/DK00/00671).

Accordingly, dopamine D$_4$ receptor ligands are potential drugs for the treatment of schizophrenia and other psychoses, and compounds with combined effects at the 5-HT transporter may have the further benefit of improved effect on depressive and negative symptoms in schizophrenic patients. Compounds with combined effect at the dopamine D$_4$ receptor and the 5-HT$_{2A}$ receptor may have the benefit of improved effect on positive and negative symptoms of schizophrenia and the benefit of effect on depressive and anxiety symptoms.

In particular, the compounds of the invention are considered useful in the treatment of positive and negative symptoms of schizophrenia without inducing extrapyramidal side effects.

SUMMARY OF THE INVENTION

The object of the present invention is to provide compounds that are partial agonists or antagonists at the dopamine D$_4$ receptor and such compounds with combined effects at the dopamine D$_4$ receptor, the 5-HT$_{2A}$ receptor, the 5-HT$_{2C}$ and/or the 5-HT transporter.

Accordingly, the present invention relates to novel compounds of the formula I

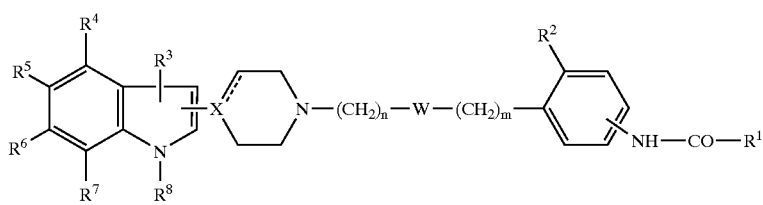

(I)

wherein R$^1$ is hydrogen or C$_{1-6}$-alkyl, C$_{2-6}$-alkenyl, C$_{2-6}$-alkynyl, C$_{3-8}$-cycloalkyl or C$_{3-8}$-cycloalkyl-C$_{1-6}$-alkyl, all of which may be substituted one or more times with substituents selected from halogen, cyano, nitro, amino, hydroxy, thiol, C$_{1-6}$-alkoxy, C$_{1-6}$-alkylthio trifluoromethyl, trifluoromethylsulfonyl and C$_{1-6}$-alkylsulfonyl, or R$^1$ is aryl, aryl-C$_{1-6}$-alkyl, heteroaryl, heteroaryl-C$_{1-6}$-alkyl where the aryl and heteroaryl groups may be substituted one or more times with substituents selected from halogen, cyano, nitro, amino, C$_{1-6}$-alkyl, C$_{1-6}$-alkoxy, C$_{1-6}$-alkylthio, hydroxy, thiol, trifluoromethyl, trifluoromethylsulfonyl and C$_{1-6}$ alkylsulfonyl, or R$^1$ is —NR'R" wherein R' and R" are independently selected from hydrogen and C$_{1-6}$-alkyl, aryl, aryl-C$_{1-6}$-alkyl, heteroaryl and heteroaryl-C$_{1-6}$-alkyl, all of which may be substituted one or more times with substituents selected from halogen, cyano, nitro, amino, C$_{1-6}$-alkyl, C$_{1-6}$ alkoxy, C$_{1-6}$-alkylthio, hydroxy, thiol, trifluoromethyl, trifluoromethylsulfonyl, and C$_{1-6}$ alkylsulfonyl, or R$^1$ is a saturated or partially saturated 5 to 6 membered ring containing one, two or three hetero atoms selected from O, S and a group N—R$^9$ wherein R$^9$ is hydrogen or C$_{1-6}$-alkyl optionally substituted with substituents selected from halogen, cyano, nitro, amino, C$_{1-6}$-alkoxy, C$_{1-6}$-alkylthio, hydroxy, thiol, trifluoromethyl, trifluoromethylsulfonyl and C$_{1-6}$ alkylsulfonyl;

W is a bond or W is an O, S, CO, CS, SO or SO$_2$ group;
n is 0–6, m is 0–6 and n+m is 0–6; provided that when W is O, or S, n≧2 and when W is CO, CS, SO or SO$_2$, n≧1;
X is C, CH or N, and the dotted line emanating from X indicates a bond when X is C and no bond when X is N or CH;
R$^2$ is C$_{1-6}$-alkyl;
R$^3$–R$^7$ are selected from hydrogen, halogen, cyano, nitro, amino, C$_{1-6}$-alkyl, C$_{2-6}$-alkenyl, C$_{2-6}$-alkynyl, C$_{3-8}$-cycloalkyl, C$_{3-8}$-cycloalkyl-C$_{1-6}$-alkyl, C$_{1-6}$-alkoxy, C$_{1-6}$-alkylthio, hydroxy, thiol, trifluoromethyl, trifluoromethylsulfonyl and C$_{1-6}$-alkylsulfonyl;
R$^8$ is hydrogen, C$_{1-6}$-alkyl, C$_{2-6}$-alkenyl, C$_{2-6}$-alkynyl, C$_{3-8}$-cycloalkyl, C$_{3-8}$-cycloalkyl-C$_{1-6}$-alkyl, aryl, aryl-C$_{1-6}$-alkyl, acyl, thioacyl, C$_{1-6}$-alkylsulfonyl, trifluoromethylsulfonyl or arylsulfonyl, or a pharmaceutically acceptable acid addition salt thereof.

In one particular embodiment, the present invention relates to compounds wherein the indole is bound to X via position 3 of the indole.

In a further embodiment, the invention relates to such compounds wherein W is a bond. In particular, the present invention relates to compounds wherein n+m is 2.

In a further embodiment, the present invention relates to such compounds wherein R$^2$ is a methyl group.

In another embodiment, the invention relates to compounds wherein the group —NH—CO—R$^1$ is attached to the phenyl group in a position para to the position of the R$^2$ group.

In particular, the present invention relates to such compounds, wherein R$^1$ is C$_{1-6}$-alkyl, C$_{3-8}$-cycloalkyl, C$_{3-8}$-cycloalkyl-C$_{1-6}$-alkyl, phenyl, phenyl-C$_{1-6}$-alkyl, furanyl, thienyl, pyridyl, pyrrolyl, pyrimidyl, wherein the phenyl groups may be substituted one or more times with substituents selected from halogen, cyano, nitro, amino, C$_{1-6}$-alkyl, C$_{1-6}$ alkoxy, C$_{1-6}$-alkylthio, hydroxy, trifluoromethyl, trifluoromethylsulfonyl and C$_{1-6}$ alkylsulfonyl, or R$^1$ is —NR'R" wherein one of R' and R" is selected from hydrogen and the other of R' and R" is selected from C$_{1-6}$-alkyl, phenyl and phenyl-C$_{1-6}$-alkyl, wherein the phenyl groups may be substituted one or more times with substituents selected from halogen, cyano, nitro, amino, C$_{1-6}$-alkyl, C$_{1-6}$ alkoxy, C$_{1-6}$-alkylthio, hydroxy, trifluoromethyl, trifluoromethylsulfonyl and C$_{1-6}$ alkylsulfonyl, or R$^1$ is a tetrahydropyranyl, morpholino, thiomorpholino, piperidino, piperazino or a N-(hydroxy-C$_{1-6}$-alkyl)piperazino group.

In a specific embodiment, the present invention relates to a compound selected from 3-(1-{2-[5-(Acetylamino)-2-methylphenyl]ethyl}piperidin-4-yl)-6-chloro-1H-indole;
3-(1-{2-[5-(Cyclobutylmethanoylamino)-2-methylphenyl]ethyl}piperidin-4-yl)-5-fluoro-1H-indole;
3-(1-{2-[5-(Acetylamino)-2-methylphenyl]ethyl}piperidin-4-yl)-5-fluoro-1H-indole;
3-(1-{2-[2-Methyl-5-(thiophen-2-ylmethanoylamino)phenyl]ethyl}piperidin-4-yl)-5-chloro-1H-indole;

3-(1-{2-[2-Methyl-5-(3-methoxybenzoylamino)phenyl]
   ethyl}piperidin-4-yl)-5-chloro-1H-indole;
3-(1-{2-[5-(Cyclopropylmethanoylamino)-2-methylphenyl]
   ethyl}piperidin-4-yl)-5-fluoro-1H-indole;
3-(1-{2-[2-Methyl-5-(thiophen-2-ylmethanoylamino)
   phenyl]ethyl}piperidin-4-yl)-5-fluoro-1H-indole;
3-(1-{2-[5-(Isobutanoylamino)-2-methylphenyl]
   ethyl}piperidin-4-yl)-5-fluoro-1H-indole;
3-(1-{2-[2-Methyl-5-(pivaloylamino)phenyl]
   ethyl}piperidin-4-yl)-5-fluoro-1H-indole;
3-(1-{2-[5-(Hexanoylamino)-2-methylphenyl]
   ethyl}piperidin-4-yl)-5-fluoro-1H-indole;
3-(1-{2-[5-(4-Fluorobenzoylamino)-2-methylphenyl]
   ethyl}piperidin-4-yl)-5-fluoro-1H-indole;
3-(1-{2-[5-(3-Methoxybenzoylamino)-2-methylphenyl]
   ethyl}piperidin-4-yl)-5-fluoro-1H-indole;
3-(1-{2-[2-Methyl-5-(pyridin-3-ylmethanoylamino)phenyl]
   ethyl}piperidin-4-yl)-5-fluoro-1H-indole;
3-(1-{2-[2-Methyl-5-(3-phenylpropanoylamino)phenyl]
   ethyl}piperidin-4-yl)-5-fluoro-1H-indole;
3-(1-{2-[2-Methyl-5-(4-methylbenzoylamino)phenyl]
   ethyl}piperidin-4-yl)-5-fluoro-1H-indole;
3-(1-{2-[2-Methyl-5-(3-Methyl-3-phenylureido)phenyl]
   ethyl}piperidin-4-yl)-6-chloro-1H-indole;
3-(1-{2-[5-(Cyclopropylmethanoylamino)-2-methylphenyl]
   ethyl}piperidin-4-yl)-6-chloro-1H-indole;
3-(1-{2-[2-Methyl-5-(thiophen-2-ylmethanoylamino)
   phenyl]ethyl}piperidin-4-yl)-6-chloro-1H-indole;
3-(1-{2-[5-(Isobutanoylamino)-2-methylphenyl]
   ethyl}piperidin-4-yl)-6-chloro-1H-indole;
3-(1-{2-[5-(3-Methoxybenzoylamino)-2-methylphenyl]
   ethyl}piperidin-4-yl)-6-chloro-1H-indole;
3-(1-{2-[2-Methyl-5-(pyridin-3-ylmethanoylamino)phenyl]
   ethyl}piperidin-4-yl)-6-chloro-1H-indole;
3-[1-(2-{5-[2-(4-Methoxyphenyl)ethanoylamino]-2-
   methylphenyl}ethyl)piperidin-4-yl]-6-chloro-1H-indole;
3-(1-{2-[2-Methyl-5-(4-methylbenzoylamino)phenyl]
   ethyl}piperidin-4-yl)-6-chloro-1H-indole;
3-[1-(2-{5-[(Cyclopentylmethanoyl)amino]-2-
   methylphenyl}ethyl)piperidin-4-yl]-6-chloro-1H-indole;
3-(1-{2-[2-Methyl-5-(morfolin-4-ylmethanoylamino)
   phenyl]ethyl}piperidin-4-yl)-5-fluoro-1H-indole;
3-[1-(2-{5-[3-(4-Fluorophenyl)ureido]-2-
   methylphenyl}ethyl)piperidin-4-yl]-5-fluoro-1H-indole;
3-(1-{2-[5-(Hexanoylamino)-2-methylphenyl]
   ethyl}piperidin-4-yl)-7-chloro-1H-indole;
3-(1-{2-[2-Methyl-5-(tetrahydropyran-4-
   ylmethanoylamino)phenyl]ethyl}piperidin-4-yl)-5-
   fluoro-1H-indole;
3-(1-{2-[5-(4-Chlorobenzoylamino)-2-methylphenyl]
   ethyl}piperidin-4-yl)-7-chloro-1H-indole;
3-(1-{2-[5-(3-Cyclohexylpropanoylamino)-2-
   methylphenyl]ethyl}piperidin-4-yl)-5-fluoro-1H-indole;
3-[1-(2-{5-[(3-Phenylpropanoyl)amino]-2-
   methylphenyl}ethyl)piperidin-4-yl]-7-chloro-1H-indole;
3-[1-(2-{5-[(2-Phenylethanoyl)amino]-2-
   methylphenyl}ethyl)piperidin-4-yl]-7-chloro-1H-indole;
3-(1-{2-[2-Methyl-5-(4-methylbenzoylamino)phenyl]
   ethyl}piperidin-4-yl)-7-chloro-1H-indole;
3-(1-{2-[5-(Cyclopropylmethanoylamino)-2-methylphenyl]
   ethyl}piperidin-4-yl)-7-chloro-1H-indole;
3-[1-(2-{5-[2-(4-Fluorophenyl)ethanoylamino]-2-
   methylphenyl}ethyl)piperidin-4-yl]-7-chloro-1H-indole;
3-[1-(2-{5-[2-(4-Methoxyphenyl)ethanoylamino]-2-
   methylphenyl}ethyl)piperidin-4-yl]-7-chloro-1H-indole;
3-[1-(2-{5-[(Cyclobutylmethanoyl)amino]-2-
   methylphenyl}ethyl)piperidin-4-yl]-7-chloro-1H-indole;
3-(1-{2-[5-(benzoylamino)-2-Methylphenyl]
   ethyl}piperidin-4-yl)-7-chloro-1H-indole;
3-(1-{2-[5-(4-Fluorobenzoylamino)-2-methylphenyl]
   ethyl}piperidin-4-yl)-7-chloro-1H-indole;
3-(1-{2-[5-(4-Methoxybenzoylamino)-2-methylphenyl]
   ethyl}piperidin-4-yl)-7-chloro-1H-indole;
3-[1-(2-{2-Methyl-5-[(pyridin-3-ylmethanoyl)amino]
   phenyl}ethyl)piperidin-4-yl]-7-chloro-1H-indole;
3-[1-(2-{2-Methyl-5-[(pyridin-4-ylmethanoyl)amino]
   phenyl}ethyl)piperidin-4-yl]-7-chloro-1H-indole;
3-[1-(2-{2-Methyl-5-[(thiophen-2-ylmethanoyl)amino]
   phenyl}ethyl)piperidin-4-yl]-7-chloro-1H-indole;
3-[1-(2-{2-Methyl-5-[(thiophen-3-ylmethanoyl)amino]
   phenyl}ethyl)piperidin-4-yl]-7-chloro-1H-indole;
3-[1-(2-{2-Methyl-5-[(1-[1,2,3]thiadiazol-5-ylmethanoyl)
   amino]phenyl}ethyl) -piperidin-4-yl]-7-chloro-1H-
   indole;
3-{1-[2-(5-Acetylamino-2-methylphenyl)-ethyl]-3,6-
   dihydro-2H-pyridin-4-yl}-5-fluoro-1H-indole;
3-[1-(2-{2-Methyl-5-[(pyridin-3-ylmethanoyl)-amino]-
   phenyl}-ethyl)-3,6-dihydro -2H-pyridin-4-yl]-5-fluoro-
   1H-indole;
3-[1-(2-{5-[(4-Fluorophenylmethanoyl)-amino]-2-
   methylphenyl}-ethyl)-3,6-dihydro -2H-pyridin-4-yl]-5-
   fluoro-1H-indole;
3-{1-[2-(5-Acetylamino-2-methylphenyl)-ethyl]-3,6-
   dihydro-2H-pyridin-4-yl}-7-chloro-1H-indole;
3-[1-(2-{2-Methyl-5-[(pyridin-3-ylmethanoyl)-amino]-
   phenyl}-ethyl)-3,6-dihydro -2H-pyridin-4-yl]-7-chloro-
   1H-indole and
3-[1-(2-{5-[(4-Fluorophenylmethanoyl)-amino]-2-
   methylphenyl}-ethyl)-3,6-dihydro -2H-pyridin-4-yl]-7-
   chloro-1H-indole or a pharmaceutically acceptable salt
   thereof.

The compounds of the invention are partial agonists or antagonists at the dopamine $D_4$ receptors. Many compounds have combined effect at dopamine $D_4$ receptors and the 5-$HT_{2A}$ receptor, the 5-$HT_{2C}$ receptor and/or 5-HT reuptake inhibiting effect.

Accordingly, the compounds of the invention are considered useful in the treatment of positive and negative symptoms of schizophrenia, other psychoses, anxiety disorders, such as generalised anxiety disorder, panic disorder and obsessive compulsive disorder, depression, aggression, side effects induced by conventional antipsychotic agents, migraine, cognitive disorders, ADHD and in the improvement of sleep.

In particular, the compounds of the invention are considered useful in the treatment of positive and negative symptoms of schizophrenia without inducing extrapyramidal side effects.

In another aspect, the present invention provides a pharmaceutical composition comprising at least one compound of formula I as defined above or a pharmaceutically acceptable acid addition salt thereof in a therapeutically effective amount and in combination with one or more pharmaceutically acceptable carriers or diluents.

In a further aspect, the present invention provides the use of a compound of formula I as defined above or an acid addition salt thereof for the manufacture of a pharmaceutical preparation for the treatment of the above mentioned disorders.

DETAILED DESCRIPTION OF THE INVENTION

The compounds of general formula I may exist as optical isomers thereof and such optical isomers are also embraced by the invention.

The term $C_{1-6}$-alkyl refers to a branched or unbranched alkyl group having from one to six carbon atoms inclusive, such as methyl, ethyl, 1-propyl, 2-propyl, 1-butyl, 2-butyl, 2-methyl-2-propyl and 2-methyl-1-propyl.

Similarly, $C_{2-6}$-alkenyl and $C_{2-6}$-alkynyl, respectively, designate such groups having from two to six carbon atoms, including one double bond and one triple bond respectively, such as ethenyl, propenyl, butenyl, ethynyl, propynyl and butynyl.

The terms $C_{1-6}$-alkoxy, $C_{1-6}$-alkylthio, $C_{1-6}$-alkylsulfonyl, $C_{1-6}$-alkylamino, $C_{1-6}$-alkylcarbonyl, and the like, designate such groups in which the alkyl group is $C_{1-6}$ alkyl as defined above. The term $C_{3-8}$-cycloalkyl designates a monocyclic or bicyclic carbocycle having three to eight C-atoms, such as cyclopropyl, cyclopentyl, cyclohexyl, etc.

Halogen means fluoro, chloro, bromo or iodo.

As used herein, the term acyl refers to a formyl, $C_{1-6}$-alkylcarbonyl, arylcarbonyl, aryl-$C_{1-6}$-alkylcarbonyl, $C_{3-8}$-cycloalkylcarbonyl or a $C_{3-8}$-cycloalkyl-$C_{1-6}$-alkyl-carbonyl group and the term thioacyl is the corresponding acyl group in which the carbonyl group is replaced with a thiocarbonyl group.

The term aryl refers to a carbocyclic aromatic group, such as phenyl, or naphthyl, in particular phenyl.

The term heteroaryl refers to 5 membered monocyclic rings such as 1H-tetrazolyl, 3H-1,2,3-oxathiazolyl, 3H-1,2,4-oxathiazolyl, 3H-1,2,5-oxathiazolyl, 1,3,2-oxathiazolyl, 1,3,4-oxathiazolyl, 1,4,2-oxathiazolyl, 3H-1,2,4-dioxazolyl, 1,3,2-dioxazolyl, 1,4,2-dioxazolyl, 3H-1,2,3-dithiazolyl, 3H-1,2,4-dithiazolyl, 1,3,2-dithiazolyl, 1,4,2-dithiazolyl, 1,2,3-oxadiazolyl, 1,2,4-oxadiazolyl, 1,2,5-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, 1H-1,2,3-triazolyl, 1H-1,2,4-triazolyl, isoxazolyl, oxazolyl, isothiazolyl, thiazolyl, 1H-imidazolyl, 1H-pyrazolyl, 1H-pyrrolyl, furanyl, thienyl, 1H-pentazole, 6-membered monocyclic rings such as 1,2,3-oxathiazinyl, 1,2,4-oxathiazinyl, 1,2,5-oxathiazinyl, 4H-1,3,5-oxathiazinyl, 1,4,2-oxathiazinyl, 1,4,3-oxathiazinyl, 1,2,3-dioxazinyl, 1,2,4-dioxazinyl, 4H-1,3,2-dioxazinyl, 4H-1,3,5-dioxazinyl, 1,4,2-dioxazinyl, 2H-1,5,2-dioxazinyl, 1,2,3-dithiazinyl, 1,2,4-dithiazinyl, 4H-1,3,2-dithiazinyl, 4H-1,3,5-dithiazinyl, 1,4,2-dithiazinyl, 2H-1,5,2-dithiazinyl, 2H-1,2,3-oxadiazinyl, 2H-1,2,4-oxadiazinyl, 2H-1,2,5-oxadiazinyl, 2H-1,2,6-oxadiazinyl, 2H-1,3,4-oxadiazinyl, 2H-1,3,5-oxadiazinyl, 2H-1,2,3-thiadiazinyl, 2H-1,2,4-thiadiazinyl, 2H-1,2,5-thiadiazinyl, 2H-1,2,6-thiadiazinyl, 2H-1,3,4-thiadiazinyl, 2H-1,3,5-thiadiazinyl, 1,2,3-triazinyl, 1,2,4-triazinyl, 1,3,5-triazinyl, 2H-1,2-oxazinyl, 2H-1,3-oxazinyl, 2H-1,4-oxazinyl, 2H-1,2-thiazinyl, 2H-1,3-thiazinyl, 2H-1,4thiazinyl, pyrazinyl, pyridazinyl, pyrimidyl, pyridyl, 2H-pyranyl, 2H-thiinyl, or bicyclic rings such as 3H-1,2,3-benzoxathiazolyl, 1,3,2-benzodioxazolyl, 3H-1,2,3-benzodithiazolyl, 1,3,2-benzodithiazolyl, benzfurazanyl, 1,2,3-benzoxadiazolyl, 1,2,3-benzothiadiazolyl, 2,1,3-benzothiadiazolyl, 1H-benzotriazolyl, 1,2-benzisoxazolyl, 2,1-benzisoxazolyl, benzoxazolyl, 1,2-benzisothiazolyl, 2,1-benzisothiazolyl, benzothiazolyl, 1H-benzimidazolyl, 1H-indazolyl, 3H-1,2-benzoxathiolyl, 1,3-benzoxathiolyl, 3H-2,1-benzoxathiolyl, 3H-1,2-benzodioxolyl, 1,3-benzodioxolyl 3H-1,2-benzodithiolyl, 1,3-benzodithiolyl, 1H-indolyl, 2H-isoindolyl, benzofuranyl, isobenzofuranyl, 1-benzothienyl, 2-benzothienyl, 1H-2,1-benzoxazinyl, 1H-2,3-benzoxazinyl, 2H-1,2-benzoxazinyl, 2H-1,3-benzoxazinyl, 2H-1,4-benzoxazinyl, 2H-3,1-benzoxazinyl, 1H-2,1-benzothiazinyl, 1H-2,3-benzothiazinyl, 2H-1,2-benzothiazinyl, 2H-1,3-benzothiazinyl, 2H-1,4-benzothiazinyl, 2H-3,1-benzothiazinyl, cinnolinyl, phtalazinyl, quinazolinyl, quinoxalinyl, isoquinolyl, quinolyl, 1H-2-benzopyranyl, 2H-1-benzopyranyl, 1H-2-benzothiopyranyl or 2H-1-benzothiopyranyl.

$R^1$ meaning a saturated or partially saturated 5- to 6-membered ring containing one or two hetero atoms selected from O, S or a group N—$R^9$ includes groups wherein $R^1$ is a group —$CR^aR^b$ and groups wherein $R^1$ is —$NR^aR^b$ wherein $R^a$ and $R^b$ together form a 5- to 6-membered saturated or partially saturated ring optionally containing an additional N—$R^9$ group or an O or S atom, e.g groups such as piperidinyl, piperazinyl, N-(hydroxy-$C_{1-6}$-alkyl)-piperazinyl, morpholinyl, thiomorpholinyl, pyrrolidinyl, tetrahydropyridyl, tetrahydropyranyl, tetrahydrofuranyl, etc.

The acid addition salts of the compounds of the invention are pharmaceutically acceptable salts formed with non-toxic acids. Exemplary of such organic salts are those with maleic, fumaric, benzoic, ascorbic, succinic, oxalic, bis-methylenesalicylic, methanesulfonic, ethanedisulfonic, acetic, propionic, tartaric, salicylic, citric, gluconic, lactic, malic, mandelic, cinnamic, citraconic, aspartic, stearic, palmitic, itaconic, glycolic, p-aminobenzoic, glutamic, benzenesulfonic, and theophylline acetic acids, as well as the 8-halotheophyllines, for example 8-bromotheophylline. Exemplary of such inorganic salts are those with hydrochloric, hydrobromic, sulfuric, sulfamic, phosphoric and nitric acids.

The pharmaceutical compositions of this invention or those which are manufactured in accordance with this invention may be administered by any suitable route, for example orally in the form of tablets, capsules, powders, syrups, etc., or parenterally in the form of solutions for injection. For preparing such compositions, methods well known in the art may be used, and any pharmaceutically acceptable carriers, diluents, excipients or other additives normally used in the art may be used.

Conveniently, the compounds of the invention are administered in unit dosage form containing said compounds in an amount of about 0.01 to 100 mg.

The total daily dose is usually in the range of about 0.05–500 mg, and most preferably about 0.1 to 50 mg of the active compound of the invention.

The compounds of the invention may be prepared as follows:

1) Alkylating a piperazine, piperidine or tetrahydropyridine of formula II with an alkylating derivative of formula III:

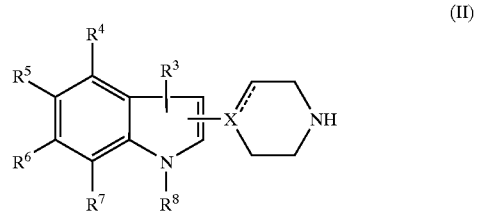

(II)

-continued

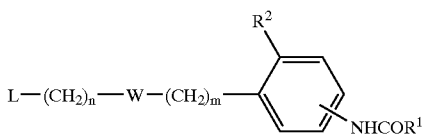

(III)

wherein $R^1$–$R^8$, X, W, n, m and the dotted line are as previously defined, and L is a leaving group such as e.g. halogen, mesylate or tosylate;

2) Reductive alkylation of an amine of formula II with a reagent of formula IV:

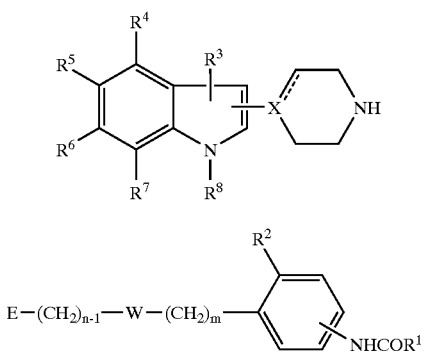

(II)

(IV)

wherein $R^1$–$R^8$, X, W, n, m and the dotted line are as previously defined, and E is an aldehyde or an activated carboxylic acid;

3) Reducing the double bond in the tetrahydropyridinyl ring in derivatives of formula V:

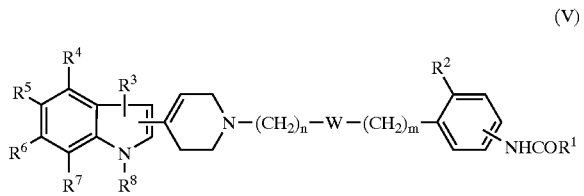

(V)

wherein $R^1$–$R^8$, W, n and m are as previously defined;

4) Acylating an amine of formula VI

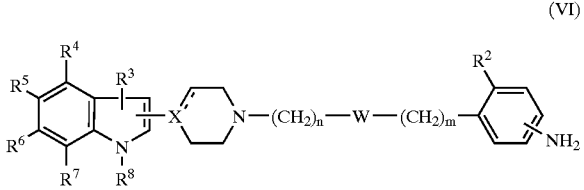

(VI)

wherein $R^1$–$R^8$, X, W, n, m and the dotted line are as previously defined by the use of a carboxylic acid and a coupling reagent, an activated ester, an acid chloride, an isocyanate, a carbamoyl chloride or a by a two-step procedure by treatment with phosgene followed by addition of an amine;

5) Cleaving a polymer bound derivative of formula VII

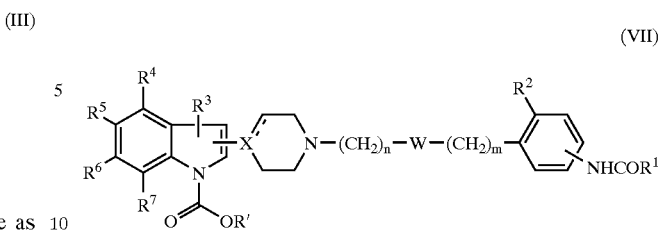

(VII)

wherein $R^1$–$R^7$, X, W, n and m are as previously defined and R'OH is hydroxyethyl or hydroxymethyl polystyrene, Wang resin or analogous polyethylene glycol polystyrene resins; whereupon the compound of Formula I is isolated as the free base or a pharmaceutically acceptable acid addition salt thereof.

The alkylation according to method 1) is conveniently performed in an inert organic solvent such as a suitably boiling alcohol or ketone, preferably in the presence of an organic or inorganic base (potassium carbonate, diisopropylethylamine or triethylamine) at reflux temperature. Alternatively, the alkylation can be performed at a fixed temperature which is different from the boiling point, in one of the above-mentioned solvents or in dimethyl formamide (DMF), dimethylsulfoxide (DMSO) or N-methylpyrrolidin-2-one (NMP), preferably in the presence of a base. The synthesis of the amines of formula II, 3-(piperidin-4-yl)-1H-indoles and 3-(3,6-dihydro-2H-pyridin-4-yl)-1H-indoles, has been described in the literature (see EP-A1-465398).

The alkylating derivatives of formula III are prepared by nitration of the alkyl-substituted phenylacetic acids followed by reduction of the nitro group, e.g. with tin(II) chloride and functionalization of the produced amino group. The carboxylic acid is subsequently reduced to the corresponding alcohol, e.g. by treatment with borane followed by conversion of the alcohol to a leaving group, e.g. by treatment with methane sulfonyl chloride or thionyl bromide.

The reductive alkylation according to method 2) is performed by standard literature methods. The reaction can be performed in two steps, e.g. coupling of amines of formula II with reagent of formula IV by standard methods via the carboxylic acid chloride, activated esters or by the use of carboxylic acids in combination with a coupling reagent such as e.g. dicyclohexyl carbodiimide, followed by reduction of the resulting amide with lithium aluminium hydride or alane. The carboxylic acid of formula IV is prepared by nitration of the alkyl-substituted phenylacetic acid followed by reduction of the nitro group, e.g. with tin(II) chloride and finally functionalization of the resulting amino group.

The reaction can also be performed by a standard one-pot procedure, e.g. using a reductive amination of amines of formula II and aldehydes of formula IV. The aldehydes of formula IV are prepared by reduction of the before mentioned functionalized (aminophenyl)acetic acid by treatment with a reducing agent such as e.g. borane. The resulting alcohol is converted to the corresponding aldehyde by standard oxidation methods, e.g. pyridinium chlorochromate.

The reduction of the double bond according to method 3) is generally performed by catalytic hydrogenation at low pressure (<3 atm.) in a Parr apparatus, or by using reducing agents such as diborane or hydroboric derivatives as produced in situ from $NaBH_4$ in trifluoroacetic acid in inert solvents such as tetrahydrofuran (THF), dioxane or diethyl ether.

The acylation according to method 4) is conveniently performed by standard methods via the carboxylic acid chloride, activated esters or by the use of carboxylic acids in combination with coupling reagents such as e.g. dicyclohexyl carbodiimide. When the acylation produces urea derivatives, the acylating reagent is carbamoyl chlorides, isocyanates or a two-step procedure consisting of treatment with phosgene followed by addition of an amine.

The intermediate compounds of formula VI are prepared as described in methods 1) and 2).

The derivatives of structure VII are prepared by means of a solid phase synthesis sequence as outlined below. The final product was cleaved from the resin according to method 5) using diluted sodium methoxide in a methanol/tetrahydrofuran mixture at ambient temperature. The first building block, VIII, prepared by tert-butoxycarbonyl protection of compounds of formula II, which is prepared by methods obvious to the chemist skilled in the art (see also EP-A1-465398), is generally attached to the resin (e.g. polystyrene bound ethyl 4-nitrophenyl carbonate) using base e.g. N,N-dimethylaminopyridine and N,N-diisopropylethylamine at elevated temperature (e.g. 50–100° C.) in an aprotic solvent (e.g. DMF or DMSO). After deprotection of compound IX by trifluoroacetic acid, the second diversifying building block is introduced by alkylation of compound X whereby compound XI is formed. The alkylating reagent is prepared by nitration of alkylsubstituted phenylacetic acid by standard nitration procedures followed by reduction of the carboxylic acid, e.g. by treatment with borane in tetrahydrofurane and finally converting the produced alcohol to a leaving group, e.g. by treatment with methanesulfonyl chloride in dichloromethane and triethylamine. The alkylation is performed at elevated temperature (50–100° C.) in an aprotic solvent such as DMF, acetone or acetonitrile leading to resin XI. After reduction of the nitro group, e.g. by treatment with tin(II) chloride in DMF, the third diversifying building block is introduced by standard acylation procedures, e.g. addition of an acid chloride, isocyanate or carbamoyl chloride and base at low temperature in DMF, dichloromethane or acetonitrile.

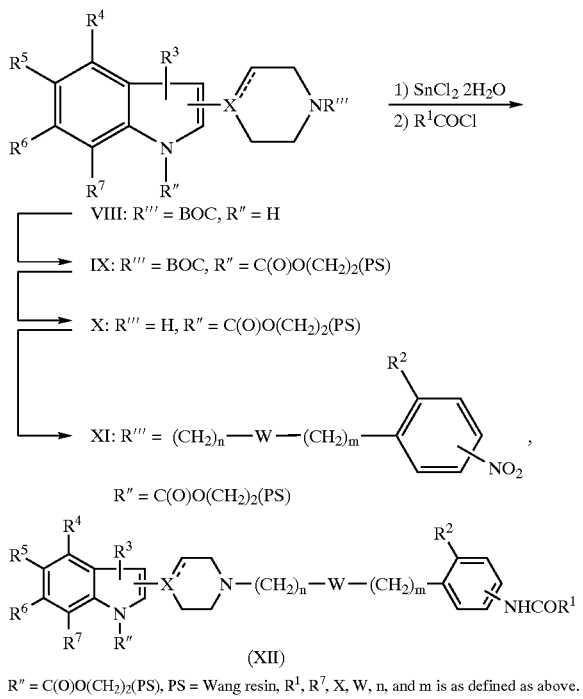

Experimental Section

Melting points were determined on a Büchi SMP-20 apparatus and are uncorrected. Analytical LC-MS data were obtained on a PE Sciex API 150EX instrument equipped with IonSpray source and Shimadzu LC-8A/SLC-10A LC system. The LC conditions (C18 column 4.6×30 mm with a particle size of 3.5 µm) were linear gradient elution with water/acetonitrile/trifluoroacetic acid (90:10:0.05) to water/acetonitrile/trifluoroacetic acid (10:90:0.03) in 4 min at 2 mL/min. Purity was determined by integration of the UV trace (254 nm). The retention times, $R_t$, are expressed in minutes.

Mass spectra were obtained by an alternating scan method to give molecular weight information. The molecular ion, MH+, was obtained at low orifice voltage (5–20V) and fragmentation at high orifice voltage (100–200V).

Preparative LC-MS-separation was performed on the same instrument. The LC conditions (C18 column 20×50 mm with a particle size of 5 µm) were linear gradient elution with water/acetonitrile/trifluoroacetic acid (80:20:0.05) to water/acetonitrile/trifluoroacetic acid (5:95:0.03) in 7 min at 22.7 mL/min. Fraction collection was performed by split-flow MS detection.

$^1$H NMR spectra were recorded at 500.13 MHz on a Bruker Avance DRX500 instrument or at 250.13 MHz on a Bruker AC 250 instrument. Deuterated chloroform (99.8% D) or dimethyl sulfoxide (99.9% D) were used as solvents. TMS was used as internal reference standard. Chemical shift values are expressed in ppm-values. The following abbreviations are used for multiplicity of NMR signals: s=singlet, d=doublet, t=triplet, q=quartet, qui=quintet, h=heptet, dd=double doublet, dt=double triplet, dq=double quartet, tt=triplet of triplets, m=multiplet. NMR signals corresponding to acidic protons are generally omitted. Content of water in crystalline compounds was determined by Karl Fischer titration. For column chromatography silica gel of type Kieselgel 60, 40–60 mesh ASTM was used. For ion-exchange chromatography (SCX, 1 g, Varian Mega Bond Elut®, Chrompack cat. no. 220776). Prior use of the SCX-columns was pre-conditioned with 10% solution of acetic acid in methanol (3 mL).

EXAMPLES

Preparation of Intermediates

A. Acylating Reagent (2-Methyl-5-nitrophenyl)acetic Acid

A 1 L round bottom flask was charged with conc. sulfuric acid (500 mL) and cooled to −12° C. (ethyleneglycol-dry ice). (2-Methylphenyl)acetic acid (35.4 g, 0.24 mol) dissolved in dichloromethane (120 mL) was added during 10 minutes and the mixture was then treated dropwise during two hours with a pre-cooled (ethylene glycol-dry ice) solution of conc. sulfuric acid (100 mL) and 100% nitric acid (10 mL). The reaction mixture was stirred for one hour at −12° C. and then poured on ice. The aqueous phase was extracted with ethyl acetate (3×1 L). The combined organic phases were washed with brine (2×1L) and water (2×1 L), dried (Na$_2$SO$_4$) and concentrated in vacuo to give the 38.1 g crude mixture (38 g). $^1$H NMR showed a 70:30 mixture of the title compound and (2-methyl-3-nitrophenyl)acetic acid, and the title compound was purified by trituration with diethyl ether.

B. Alkylating Reagents 2-(2-Methanesulfonyloxyethyl)-1-methyl-4-nitrobenzene

A 500 mL round bottom flask was charged with (2-methyl-5-nitrophenyl)acetic acid (15 g, 77 mmol) and dry THF (300 mL). The mixture was cooled on ice-water and treated dropwise with borane-tetrahydrofurane complex (90 mL, 1M in THF, 90 mmol) during one hour. The reaction mixture was stirred for two hours at room temperature and then poured on ice. The aqueous phase was extracted with ethyl acetate (3×600 mL). The combined organic phases were washed with brine (2×1L) and water (2×1L), dried ($Na_2SO_4$) and concentrated in vacuo. The residue was redissolved in dichloromethane (200 mL) and triethylamine (10.8 mL, 78 mmol). The mixture was cooled on ice-water and a mixture of methanesulfonyl chloride (6.05 mL, 78 mmol) dissolved in dichloromethane (100 mL) was added dropwise during 20 minutes. The reaction mixture was stirred for 2 hours at room temperature. The reaction mixture was concentrated in vacuo. The residue was purified by flash chromatography on silicagel (eluent:ethyl acetate/heptane 2:3) to give the title compound (7.8 g). $^1H$ NMR ($CDCl_3$): 2.45 (s, 3H); 2.96 (s, 3H); 3.15 (t, 2H); 4.45 (t, 2H); 7.33 (d, 1H); 7.98–8.11 (m, 2H).

2-(2-Bromoethyl)-1-methyl-4-nitrobenzene

A mixture of 2-(2-methanesulfonyloxyethyl)-1-methyl-4-nitrobenzene (4.0 g) and lithium bromide (6.6 g) in acetone (250 mL) was boiled under reflux for 3½ h. The resulting mixture was cooled and filtered. The residue was purified by flash chromatography on silicagel (eluent:ethyl acetate/heptane 1:2) to give the title compound (3.7 g). $^1H$ NMR (DMSO-$d_6$): 2.45 (s, 3H); 3.25 (t, 2H); 3.80 (t, 2H); 7.50 (d, 1H); 8.05 (dd, 1H); 8.15 (d, 1H).

Preparation of Solid Supported Intermediates

Preparation of 4-nitrophenyloxycarbonyloxyethyl Polystyrene

A 2 L round bottom flask was charged with hydroxyethyl polystyrene (62.9 g, 83 mmol, commercially available from Rapp Polymere, cat. no. HA 1 400 00), N-methylmorpholine (20 mL, 183 mmol), and dry dichloromethane (900 mL). The suspension was cooled on an ice bath followed by the addition over a period of 5 min of 4-nitrophenyl chloroformiate, dissolved in dry dichloromethane (400 mL). The mixture was stirred at room temperature for 16 h. The resin was filtered off and washed with dry dichloromethane (5×200 mL). The resin was dried in vacuo (20° C., 72 h) to yield the title resin (79.6 g).

Preparation of Polymer Bound 3-{1-[2-(5-amino-2-methylphenyl)ethyl]piperidin-4-yl}-5-fluoro-1H-indole A 100 mL round bottom flask was charged with 4-nitrophenyloxycarbonyloxyethyl polystyrene (6.6 g, 7.1 mmol), 5-fluoro-3-(1-tert-butoxycarbonylpiperidin-4-yl)-1H-indole (2.7 g, 8.1 mmol), diisopropylethylamine (6.2 mL, 35.6 mmol), 4-dimethylaminopyridine (0.87 g, 7.1 mmol), and dry dimethyl formamide (85 mL). The mixture was stirred at 90° C. for 20 h. After cooling to room temperature, the resin was filtered off and washed with dry dimethyl formamide (3×25 mL), dry acetonitrile (3×25 mL) and dry dichloromethane (3×25 mL). The resin was transferred to a 250 mL glass cylinder with a fritte and a three way junction in the bottom. The resin was then treated for 20 min with 80 mL of a 1:1 mixture of dichloromethane and trifluoroacetic acid containing anisole (2%, w/w) and methionine (0.2%, w/w), using a flow of nitrogen to agitate the resin (Caution: Generation of carbon dioxide). The resin was filtered off and washed with dry dichloromethane (25 mL), a 1:1 mixture of dichloromethane:triethylamine (3×25 mL) and dry dichloromethane (3×25 mL). The resin was transferred to a 250 mL round bottom flask. Acetonitrile (70 mL), diisopropylethylamine (5.2 mL, 30 mmol) and 2-(2-methanesulfonyloxyethyl)-1-methyl-4-nitrobenzene (3.67 g, 14 mmol) was added. The reaction mixture was heated to 70° C. for 18 h. After cooling to room temperature, the resin was filtered off and washed with dry acetonitrile (3×25 mL) and dry dichloromethane (3×25 mL). The resin was transferred to a 250 mL round bottom flask and treated with tin(II) chloride dihydrate (60 mL of an 0.5 M solution in DMF). The reaction mixture was stirred for 18 h. at room temperature. The resin was filtered off and washed with dry dimethyl formamide (3×25 mL), dry acetonitrile (3×25 mL) and dry dichloromethane (3 ×25 mL). The resin was dried in vacuo (20° C., 20 h) to yield the title resin (6.3 g).

The following polymer bound compounds were prepared in a similar manner:

3-{1-[2-(5-amino-2-methylphenyl)ethyl]piperidin-4-yl}-5-chloro-1H-indole

3-{1-[2-(5-amino-2-methylphenyl)ethyl]piperidin-4-yl}-6-chloro-1H-indole

3-{1-[2-(5-amino-2-methylphenyl)ethyl]piperidin-4-yl}-7-chloro-1H-indole

Preparation of the Compounds of the Invention

Example 1

1a, 3-(1-{2-[5-(Acetylamino)-2-methylphenyl]ethyl}piperidin-4-yl)-6-chloro-1H-indole, fumarate A mixture of (2-methyl-5-nitrophenyl)acetic acid (47 g) and thionyl chloride (62 mL) in dichloromethane (400 mL) was boiled under reflux for 5 h and concentrated in vacuo. A small amount of the residue (5 g) was dissolved in tetrahydrofuran (100 mL) and added dropwise to a mixture of 6-chloro-3-(3,6-dihydro-2H-pyridin-4-yl)-1H-indole (6.0 g) and triethylamine (5 mL) in tetrahydrofuran (250 mL) at 0° C. over a period of 10 min. The mixture was concentrated in vacuo, aqueous 2 N sodium hydroxide (400 mL) and ethyl acetate (400 mL) was added, whereby 6-chloro-3-{1-[2-(2-methyl-5-nitrophenyl)-1-oxoethyl]-3,6-dihydro-2H-pyridin-4-yl}-1H-indole precipitated and was collected by filtration (3.7 g). The organic phases were isolated, washed with brine, dried ($Na_2SO_4$), filtered and concentrated in vacuo. The residue was purified by flash chromatography on silicagel (eluent:ethyl acetate/heptane 2:1) to give another batch of 6-chloro-3-{1-[2-(2-methyl-5-nitrophenyl)-1-oxoethyl]-3,6-dihydro-2H-pyridin-4-yl}-1H-indole (2.2 g). A mixture of 6-chloro-3-{1-[2-(2-methyl-5-nitrophenyl)-1-oxoethyl]-3,6-dihydro-2H-pyridin-4-yl}-1H-indole (5.3 g) in tetrahydrofuran (100 mL) and tin(II) chloride dihydrate (14.5 g) in ethanol (150 mL) was boiled under reflux for 2 h, and the solvent reduced to about 100 mL in vacuo. Aqueous ammonia was added and the organic phase was removed in vacuo. The aqueous phase was extracted with ethyl acetate, and the combined organic phases were washed with brine, dried ($Na_2SO_4$), filtered and concentrated in vacuo to give 6-chloro-3-{1-[2-(5-amino-2-methylphenyl)-1-oxoethyl]-3,6-dihydro-2H-pyridin-4-yl}-1H-indole (5.1 g). This compound was dissolved in tetrahydrofuran (200 mL) and added dropwise to a suspension of lithium aluminium hydride (1.5 g) in tetrahydrofuran (100 mL) at 10° C. over a period of 15 min. The resulting mixture was stirred at room temperature for 16 h and subjected to a standard work up procedure to give crude 6-chloro-3-{1-[2-(5-amino-2-methylphenyl)ethyl]-3,6-dihydro-2H-pyridin-4-yl}-1H-indole (7.5 g, includes tetrahydrofuran). Crude compound (4.0 g) was dissolved in acetic acid (100 mL) followed by the addition of platinum oxide (400 mg), and the resulting mixture was shaken under 3 atmosphere hydrogen pressure for 6 h at room temperature. The mixture was filtered and added water (400 mL) followed by the addition of aqueous ammonia to basic pH. The aqueous phase was extracted with an ethyl acetate, and the combined organic phase was washed with brine, dried ($Na_2SO_4$), filtered and concentrated in vacuo to give 6-chloro-3-{1-[2-(5-amino-2-methylphenyl)ethyl]piperidin-4-yl}-1H-indole (2.4 g). The compound was dissolved in tetrahydrofuran (200 mL) and triethylamine (1 mL), and the mixture was cooled to 0° C. followed by dropwise addition of acetyl chloride (0.5 mL) in dichloromethane (30 mL). The resulting mixture was stirred at room temperature for 2 h, filtered and concentrated in vacuo. The residue was purified by flash chromatography on silicagel (eluent:ethyl acetate/ethanol/triethylamine 80:20.4) to give crude title compound that was collected as the fumerate salt from ethanol (0.7 g). Mp 164–166° C. $^1$H NMR (DMSO-d$_6$): 1.85–2.10 (m, 4H); 2.25 (s, 3H); 2.65–3.00 (m, 7H); 3.30–3.45 (m, 2H); 6.60 (s, 3H (fumerate)); 7.00 (dd, 1H); 7.10 (d, 1H); 7.20 (d, 1H); 7.30–7.45 (m, 3H); 7.65 (d, 1H); 9.85 (s, 1H); 11.05 (s, 1H). MS m/z: 410 (MH+), 259, 247, 176.

Example 2

2a, 3-(1-{2-[5-Cyclobutylmethanoylamino)-2-methylphenyl]ethyl}piperidin-4-yl)-5-fluoro-1H-indole, oxalate A mixture of 5-fluoro-3-(piperidin-4-yl)-1H-indole (2.7 g) in dimethyl formamide (75 mL), 2-(2-bromoethyl)-1-methyl-4-nitrobenzene (3.7 g) in butanone (200 mL) and triethylamine (9.3 mL) was boiled under reflux for 20 h, and the resulting mixture was concentrated in vacuo. The residue was purified by flash chromatography on silicagel (eluent:ethyl acetate/triethylamine 100:4) to give 5-fluoro-3-{1-[2-(2-methyl-5-nitrophenyl)ethyl]piperidin-4-yl}-1H-indole (3.6 g), which subsequently was dissolved in acetic acid (25 ml) followed by the addition of ethanol (75 mL) and platinum oxide (50 mg). The resulting mixture was shaken under 3 atmosphere hydrogen pressure for 3 h at room temperature. The mixture was reduced in vacuo (50 mL), poured onto an ice/water mixture followed by the addition of aqueous ammonia to basic pH. The aqueous phase was extracted with an ethyl acetate/tetrahydrofuran mixture, and the combined organic phase was washed with brine, dried (MgSO$_4$), filtered and concentrated in vacuo. The residue was purified by flash chromatography on silicagel (eluent:ethyl acetate/ethanol/triethylamine 100:4:4) to give 3-{1-[2-(5-amino-2-methylphenyl)ethyl]piperidin-4-yl}-5-fluoro-1H-indole (1.0 g), which subsequently was dissolved in tetrahydrofuran (45 mL) and triethylamine (1.3 mL) at 5° C. followed by the addition of cyclobutancarbonyl chloride (0.3 g) in tetrahydrofuran (15 mL). The resulting mixture was stirred at 5° C. for 1 h, filtered and concentrated in vacuo. The residue was purified by flash chromatography on silicagel (eluent:ethyl acetate/ethanol/triethylamine 100:4:4) to give the crude product that was isolated as the oxalate salt from ethyl acetate as a white crystalline compound (0.7 g). Mp 116–125° C. $^1$H NMR (DMSO-d$_6$): 1.75–1.85 (m, 1H); 1.85–2.05 (m, 3H); 2.05–2.25 (m, 6H); 2.30 (s, 3H); 2.90–3.25 (m, 8H); 3.65 (d, 2H); 6.85–6.95 (m, 1H); 7.10 (d, 1H); 7.25 (s, 1H); 7.30–7.40 (m, 2H); 7.40 (d, 1H); 7.55 (s, 1H); 9.65 (s, 1H); 11.00 (s, 1H). MS m/z: 434 (MH+).

Example 3

3a, 3-(1-{2-[5-(Acetylamino)-2-methylphenyl]ethyl}piperidin-4-yl)-5-fluoro-1H-indole Polymer bound 3-[1-(2-{5-amino-2-methylphenyl}ethyl)piperidin-4-yl]-5-fluoro-1H-indole (100 mg, 100 μmol), triethylamine (90 μL), and dimethylaminopyridine (0.50 mL of an 0.2 M solution in dry acetonitrile) were mixed in a reactor tube. The mixture was cooled to 0° C. and treated with acetyl chloride (0.50 mL of an 1M solution in dry acetonitrile). The reaction mixture was left at 0° C. for 2 h. The resin was filtered off and washed with dry acetonitrile (3×1 mL). The resin was treated for 1 h with 1 mL of a mixture of sodium methoxide (2 mL, 5 N sodium methoxide in methanol), methanol (50 mL) and tetrahydrofuran (50 mL). After filtration, the resin was washed with methanol (1 mL). The combined filtrates were loaded on a pre-conditioned ion exchange column (500 mg SCX column, commercially available from Analytical Instruments, part no. 1210–2040), washed with acetonitrile (1 mL) and methanol (1 mL). The product was eluted with 4 M ammonia in methanol. Evaporation of volatile solvents afforded the title compound as a yellow oil (6 mg, 15 μmol). LC/MS (m/z) 394 (MH+), RT=1.98, purity: 88%.

The following compounds were prepared in similar manner. When ureas were prepared, the corresponding carbamoyl chloride was used in place of an acid chloride. The compounds were purified by preparative reversed phase HPLC chromatography if the UV trace (254 nm) showed less than 70% purity of the expected mass. The resulting solution was subsequently loaded on a pre-conditioned ion exchange column washed with acetonitrile (1 mL) and methanol (1 mL). The product was eluted with 4 M ammonia in methanol and the solution concentrated in vacuo to yield the final product.

3b, 3-(1-{2-[2-Methyl-5-(thiophen-2-ylmethanoylamino)phenyl]ethyl}piperidin-4-yl)-5-chloro-1H-indole: LC/MS (m/z) 478 (MH+), RT=2.45, purity: 74%.

3c, 3-(1-{2-[2-Methyl-5-(3-methoxybenzoylamino)phenyl]ethyl}piperidin-4-yl)-5-chloro-1H-indole: LC/MS (m/z) 502 (MH+), RT=2.51, purity: 86%.

3d, 3-(1-{2-[5-(Cyclopropylmethanoylamino)-2-methylphenyl]ethyl}piperidin-4-yl)-5-fluoro-1H-indole: LC/MS (m/z) 420 (MH+), RT=2.16, purity: 97%.

3e, 3-(1-{2-[2-Methyl-5-(thiophen-2-ylmethanoylamino)phenyl]ethyl}piperidin-4-yl)-5-fluoro-1H-indole: LC/MS (m/z) 462 (MH+), RT=2.33, purity: 91%.

3f, 3-(1-{2-[5-(Isobutanolamino)-2-methylphenyl]ethyl}piperidin-4-yl)-5-fluoro-1H-indole: LC/MS (m/z) 422 (MH+), RT=2.20, purity: 93%.

3g, 3-(1-{2-[2-Methyl-5-(pivaloylamino)phenyl]ethyl}piperidin-4-yl)-5-fluoro-1H-indole: LC/MS (m/z) 436 (MH+), RT=2.33, purity: 95%.

3h, 3-(1-{2-[5-(Hexanoylamino)-2-methylphenyl]ethyl}piperidin-4-yl)-5-fluoro-1H-indole: LC/MS (m/z) 450 (MH+), RT=2.48, purity: 95%.

3i, 3-(1-{2-[5-(4-Fluorobenzoylamino)-2-methylphenyl]ethyl}piperidin-4-yl)-5-fluoro-1H-indole: LC/MS (m/z) 474 (MH+), RT=4.02, purity: 95%.

3j, 3-(1-{2-[5-(3-Methoxybenzoylamino)-2-methylphenyl]ethyl}piperidin-4-yl)-5-fluoro-1H-indole: LC/MS (m/z) 486 (MH+), RT=2.41, purity: 91%.

3k, 3-(1-{2-[2-Methyl-5-(pyridin-3-ylmethanoylamino)phenyl]ethyl}piperidin-4-yl)-5-fluoro-1H-indole: LC/MS (m/z) 457 (MH+), RT=1.90, purity: 80%.

3l, 3-(1-{2-[2-Methyl-5-(3-phenylpropanoylamino)phenyl]ethyl}piperidin-4-yl)-5-fluoro-1H-indole: LC/MS (m/z) 484 (MH+), RT=2.47, purity: 96%.

3m, 3-(1-{2-[2-Methyl-5-(4-methylbenzoylamino)phenyl]ethyl}piperidin-4-yl)-5-fluoro-1H-indole: LC/MS (m/z) 470 (MH+), RT=2.47, purity: 90%.

3n, 3-(1-{2-[2-Methyl-5-(3-Methyl-3-phenylureido)phenyl]ethyl}piperidin-4-yl)-6-chloro-1H-indole: LC/MS (m/z) 501 (MH+), RT=2.51, purity: 87%.

3o, 3-(1-{2-[5-(Cyclopropylmethanoylamino)-2-methylphenyl]ethyl}piperidin-4-yl)-6-chloro-1H-indole: LC/MS (m/z) 436 (MH+), RT=2.30, purity: 96%.

3p, 3-(1-{2-[2-Methyl-5-(thiophen-2-ylmethanoylamino)phenyl]ethyl}piperidin-4-yl)-6-chloro-1H-indole: LC/MS (m/z) 478 (MH+), RT=2.44, purity: 93%.

3q, 3-(1-{2-[5-(Isobutanoylamino)-2-methylphenyl]ethyl}piperidin-4-yl)-6-chloro-1H-indole: LC/MS (m/z) 438 (MH+), RT=2.33, purity: 96%.

3r, 3-(1-{2-[5-(3-Methoxybenzoylamino)-2-methylphenyl]ethyl}piperidin-4-yl)-6-chloro-1H-indole: LC/MS (m/z) 502 (MH+), RT=2.51, purity: 93%.

3s, 3-(1-{2-[2-Methyl-5-(pyridin-3-ylmethanoylamino)phenyl]ethyl}piperidin-4-yl)-6-chloro-1H-indole: LC/MS (m/z) 473 (MH+), RT=2.03, purity: 88%.

3t, 3-[1-(2-{5-[2-(4-Methoxyphenyl)ethanoylamino]-2-methylphenyl}ethyl)piperidin-4-yl]-6-chloro-1H-indole: LC/MS (m/z) 516 (MH+), RT=2.52, purity: 94%.

3u, 3-(1-{2-[2-Methyl-5-(4-methylbenzoylamino)phenyl]ethyl}piperidin-4-yl)-6-chloro-1H-indole: LC/MS (m/z) 486 (MH+), RT=2.58, purity: 93%.

3v, 3-[1-(2-{5-[(Cyclopentylmethanoyl)amino]-2-methylphenyl}ethyl)piperidin-4-yl]-6-chloro-1H-indole: LC/MS (m/z) 465 (MH+), RT=2.49, purity: 95%.

3x, 3-(1-{2-[2-Methyl-5-(morfolin-4-ylmethanoylamino)phenyl]ethyl}piperidin-4-yl)-5-fluoro-1H-indole: LC/MS (m/z) 465 (MH+), RT=3.27, purity: 91%.

3y, 3-[1-(2-{5-[3-(4-Fluorophenyl)ureido]-2-methylphenyl}ethyl)piperidin-4-yl]-5-fluoro-1H-indole: LC/MS (m/z) 504 (MH+), RT=2.52, purity: 92%.

3z, 3-(1-{2-[5-(Hexanoylamino)-2-methylphenyl]ethyl}piperidin-4-yl)-7-chloro-1H-indole: LC/MS (m/z) 466 (MH+), RT=2.55, purity: 88%.

3aa, 3-(1-{2-[2-Methyl-5-(tetrahydropyran-4-ylmethanoylamino)phenyl]ethyl}piperidin-4-yl)-5-fluoro-1H-indole: LC/MS (m/z) 464 (MH+), RT=2.05, purity: 96%.

3ab, 3-(1-{2-[5-(4-Chlorobenzoylamino)-2-methylphenyl]ethyl}piperidin-4-yl)-7-chloro-1H-indole: LC/MS (m/z) 506 (MH+), RT=2.62, purity: 87%.

3ac, 3-(1-{2-[5-(3-Cyclohexylpropanoylamino)-2-methylphenyl]ethyl}piperidin-4-yl)-5-fluoro-1H-indole: LC/MS (m/z) 490 (MH+), RT=2.76, purity: 95%.

3ad, 3-[1-(2-{5-[(3-Phenylpropanoyl)amino]-2-methylphenyl}ethyl)piperidin-4-yl]-7-chloro-1H-indole: LC/MS (m/z) 500 (MH+), RT=2.56, purity: 91%.

3ae, 3-[1-(2-{5-[(2-Phenylethanoyl)amino]-2-methylphenyl}ethyl)piperidin-4-yl]-7-chloro-1H-indole: LC/MS (m/z) 486 (MH+), RT=2.48, purity: 92%.

3af, 3-(1-{2-[2-Methyl-5-(4-methylbenzoylamino)phenyl]ethyl}piperidin-4-yl)-7-chloro-1H-indole: LC/MS (m/z) 486 (MH+), RT=2.54, purity: 89%.

3ag, 3-(1-{2-[5-(Cyclopropylmethanoylamino)-2-methylphenyl]ethyl}piperidin-4-yl)-7-chloro-1H-indole: LC/MS (m/z) 436 (MH+), RT=2.26, purity: 93%.

Example 4

4a, 3-[1-(2-{5-[2-(4-Fluorophenyl)ethanoylamino]-2-methylphenyl}ethyl)piperidin-4-yl]-7-chloro-1H-indole A mixture of (2-methyl-5-nitrophenyl)acetic acid (2.5 g) and 1,1'-carbonyldiimidazole (2.1 g) in dimethyl formamide (50 mL) was stirred at room temperature for 15 min and subsequently added a solution of 7-chloro-3-(piperidin-4-yl)-1H-indole (3.0 g) in dimethyl formamide (50 mL). The resulting mixture was stirred at room temperature for 1 h and poured onto an ice/water mixture. The compound was isolated by filtration and dissolved in tetrahydrofuran. The organic phase was washed with brine, dried (MgSO$_4$), filtered and concentrated in vacuo to give 7-chloro-3-{1-[2-(2-methyl-5-nitrophenyl)-1-oxoethyl]-piperidin-4-yl}-1H-indole (4.7 g). A mixture of 7-chloro-3-{1-[2-(2-methyl-5-nitrophenyl)-1-oxoethyl]-piperidin-4-yl}-1H-indole (16.6 g) and ethanol (500 mL) was heated to reflux temperature and subsequently added concentrated HCl (22 mL) and iron powder (11.3 g) over a period of 30 min. The resulting mixture was boiled under reflux for an additional 90 min, filtered hot and concentrated in vacuo. The residue was dissolved in tetrahydrofuran, and the organic phase was washed with brine, dried (MgSO$_4$), filtered and concentrated in vacuo to give give 7-chloro-3-{1-[2-(5-amino-2-methylphenyl)-1-oxoethyl]-piperidin-4-yl}-1H-indole (14.3 g). A suspension of lithium aluminium hydride (6.4 g) in tetrahydrofuran (250 mL) was cooled (5° C.) and subsequently added a mixture of 7-chloro-3-{1-[2-(5-amino-2-methylphenyl)-1-oxoethyl]-piperidin-4-yl}-1H-indole (16.0 g) in tetrahydrofuran (250 mL). The resulting mixture was boiled under reflux for 90 min, cooled to 5° C. and quenched by the addition of water. The mixture was dried (MgSO$_4$), stirred for 10 min, filtered and concentrated in vacuo to give 7-chloro-3-{1-[2-(5-amino-2-methylphenyl)ethyl]piperidin-4-yl}-1H-indole (12.4 g). A solution of 7-chloro-3-{1-[2-(5-amino-2-methylphenyl)ethyl]piperidin-4-yl}-1H-indole (1.0 g) and N-ethyldiisopropylamine (0.7 g) in tetrahydrofuran (25 mL) was cooled (5° C.) and subsequently added a solution of (4-fluorophenyl)acetyl chloride in tetrahydrofuran (25 mL). The resulting mixture was stirred at room temperature for 1 h and subsequently poured onto brine. The aqueous phase was extracted with tetrahydrofuran, and the combined organic phases were dried (MgSO$_4$), filtered and concentrated in vacuo. The residue was purified by flash chromatography on silicagel (eluent:ethyl acetate/heptane/triethylamine 70:30:5) to give the product (0.81 g). LC/MS (m/z) 504 (MH+), RT=2.45, purity: 62%.

The following compounds were prepared in a similar manner 4b, 3-[1-(2-{5-[2-(4-Methoxyphenyl)ethanoylamino]-2-methylphenyl}ethyl)piperidin-4-yl]-7-chloro-1H-indole from 7-chloro-3-{1-[2-(5-amino-2-methylphenyl)ethyl]piperidin-4-yl}-1H-indole and (4-methoxyphenyl)acetyl chloride. LC/MS (m/z) 516 (MH+), RT=2.35, purity: 61%.

4c, 3-[1-(2-{5-[(Cyclobutylmethanoyl)amino]-2-methylphenyl}ethyl)piperidin-4-yl]-7-chloro-1H-indole from 7-chloro-3-{1-[2-(5-amino-2-methylphenyl)ethyl]piperidin-4-yl}-1H-indole and cyclobutanecarbonyl chloride. LC/MS (m/z) 450 (MH+), RT=2.19, purity: 62%.

4d, 3-(1-{2-[5-(benzoylamino)-2-Methylphenyl]ethyl}piperidin-4-yl)-7-chloro-1H-indole from 7-chloro-3-{1-[2-(5-amino-2-methylphenyl)ethyl]piperidin-4-yl}-1H-indole and benzoyl chloride. LC/MS (m/z) 472 (MH+), RT=2.47, purity: 94%.

4e, 3-(1-{2-[5-(4-Fluorobenzoylamino)-2-methylphenyl]ethyl}piperidin-4-yl)-7-chloro-1H-indole from 7-chloro-3-{1-[2-(5-amino-2-methylphenyl)ethyl]piperidin-4-yl}-1H-indole and 4-fluorobenzoyl chloride. LC/MS (m/z) 490 (MH+), RT=2.40, purity: 74%.

4f, 3-(1-{2-[5-(4-Methoxybenzoylamino)-2-methylphenyl]ethyl}piperidin-4-yl)-7-chloro-1H-indole from 7-chloro-3-{1-[2-(5-amino-2-methylphenyl)ethyl]piperidin-4-yl}-1H-indole and 4-methoxybenzoyl chloride. LC/MS (m/z) 502 (MH+), RT=2.39, purity: 85%.

4g, 3-[1-(2-{2-Methyl-5-[(pyridin-3-ylmethanoyl)amino]phenyl}ethyl)piperidin-4-yl]-7-chloro-1H-indole from 7-chloro-3-{1-[2-(5-amino-2-methylphenyl)ethyl]piperidin-4-yl}-1H-indole and nicotinoyl chloride. LC/MS (m/z) 473 (MH+), RT=1.85, purity: 75%.

4h, 3-[1-(2-{2-Methyl-5-[(pyridin-4-ylmethanoyl)amino]phenyl}ethyl)piperidin-4-yl]-7-chloro-1H-indole from 7-chloro-3-{1-[2-(5-amino-2-methylphenyl)ethyl]piperidin-4-yl}-1H-indole and isonicotinoyl chloride. LC/MS (m/z) 473 (MH+), RT=1.84, purity: 80%.

4i, 3-[1-(2-{2-Methyl-5-[(thiophen-2-ylmethanoyl)amino]phenyl}ethyl)piperidin-4-yl]-7-chloro-1H-indole from 7-chloro-3-{1-[2-(5-amino-2-methylphenyl)ethyl]piperidin-4-yl}-1H-indole and thiophene-2-carbonyl chloride. LC/MS (m/z) 478 (MH+), RT=2.34, purity: 95%.

4j, 3-[1-(2-{2-Methyl-5-[(thiophen-3-ylmethanoyl)amino] phenyl}ethyl)piperidin-4-yl]-7-chloro-1H-indole from 7-chloro-3-{1-[2-(5-amino-2-methylphenyl)ethyl] piperidin-4-yl}-1H-indole and thiophene-3-carbonyl chloride. LC/MS (m/z) 478 (MH+), RT=2.31, purity: 77%.

4k, 3-[1-(2-{2-Methyl-5-[(1-[1,2,3]thiadiazol-5-ylmethanoyl)amino]phenyl}ethyl)piperidin-4-yl]-7-chloro-1H-indole from 7-chloro-3-{1-[2-(5-amino-2-methylphenyl)ethyl]piperidin-4-yl}-1H-indole and [1,2,3]thiadiazol-5-carbonyl chloride. LC/MS (m/z) 480 (MH+), RT=2.24, purity: 69%.

Pharmacological Testing

The compounds of the invention were tested in well-recognised and reliable tests. The tests were as follows:

Inhibition of the Binding of [$^3$H]YM-09151-2 to Human Dopamine $D_4$ Receptors By this method, the inhibition by drugs of the binding of [$^3$H]YM-09151-2 (0.06 nM) to membranes of human cloned dopamine $D_{4.2}$ receptors expressed in CHO-cells is determined in vitro. The method is modified from NEN Life Science Products, Inc., technical data certificate PC2533-10/96. In table 1 below, the test results are shown:

TABLE 1

Binding Data (% inhibition of binding at 50 nM).

| Compound | % inhib. |
|---|---|
| 3a | 83 |
| 3b | 86 |
| 3c | 68 |
| 3d | 89 |
| 3e | 89 |
| 3f | 96 |
| 3g | 86 |
| 3h | 83 |
| 3j | 90 |
| 3k | 91 |
| 3l | 74 |
| 3m | 81 |
| 3n | 76 |
| 3o | 99 |
| 3p | 92 |
| 3q | 97 |
| 3r | 88 |
| 3s | 92 |
| 3t | 75 |
| 3u | 86 |
| 3v | 95 |
| 3x | 90 |
| 3y | 83 |
| 3z | 91 |
| 3aa | 96 |
| 3ab | 79 |
| 3ac | 97 |
| 3ad | 83 |
| 3ae | 89 |
| 3af | 90 |
| 3ag | 95 |
| 4a | 23[a] |
| 4b | 16[a] |
| 4c | 5[a] |
| 4d | 48 |
| 4e | 44 |
| 4f | 48 |
| 4g | 6[a] |
| 4h | 73 |
| 4i | 85 |
| 4j | 48 |
| 4k | 67 |

[a]IC$_{50}$ value

The compounds of the invention have been found potently to inhibit the binding of tritiated YM-09151-2 to dopamine $D_4$ receptors.

The compounds have also been tested in a functional assay described by Gazi et al. in Br. J. Pharmacol. 1999, 128, 613–629. In this test, the compounds were shown to be partial agonists or antagonists at dopamine $D_4$ receptors.

The compounds of the invention have also been tested in the following tests:

Inhibition of the Binding of [$^3$H]Spiperone to $D_2$ Receptors

The compounds were tested with respect to affinity for the dopamine $D_2$ receptor by determining their ability to inhibit the binding of [$^3$H]Spiperone to $D_2$ receptors by the method of Hyttel et al. J. Neurochem. 1985, 44, 1615.

Inhibition of the Uptake of [$^3$H]Serotonin into Whole Rat Brain Synaptosomes

The compounds were tested with respect to their 5-HT reuptake inhibiting effect by measuring their ability to inhibit the uptake of [$^3$H]Serotonin into whole rat brain synaptosomes in vitro. The assay was performed as described by Hyttel Psychopharmacology 1978, 60, 13.

Inhibition of the Binding of [$^3$H]Ketanserin to 5-HT$_{2A}$ Receptors

The compounds were tested with respect to their affinity for 5-HT$_{2A}$ receptors by determining their ability to inhibit the binding of [$^3$H]Ketanserin (0.50 nM) to membranes from rat brain (cortex) in vitro. Method described in Sánchez et al. Drug Dev. Res. 1991, 22, 239–250.

5-HT$_{2C}$ Receptor Efficacy as Determined by Fluorometry

The compounds were tested with respect to their efficacy on 5-HT$_{2C}$ receptor-expressing CHO cells as determined by fluorometric imaging plate reader (FLIPR) analysis. This assay was carried out according to Molecular Devices Inc. instructions for their FLIPR Calcium Assay Kit and as modified from Porter et al. Br. J. Pharmacol. 1999, 128, 13.

The compounds were found to have no substantial or only weak affinity for the dopamine $D_2$ receptor. Many of the compounds were also found to have affinity for 5-HT$_{2A}$ receptors and serotonin reuptake inhibiting activity.

Thus, the compounds of the invention are considered useful in the treatment of positive and negative symptoms of schizophrenia, other psychoses, anxiety disorders, such as generalised anxiety disorder, panic disorder and obsessive compulsive disorder, depression, side effects induced by conventional antipsychotic agents, migraine, and in the improvement of sleep. In particular the compounds of the invention are considered useful in the treatment of positive and negative symptoms of schizophrenia without inducing extrapyramidal side effects.

Formulation Examples

The pharmaceutical formulations of the invention may be prepared by conventional methods in the art.

For example: Tablets may be prepared by mixing the active ingredient with ordinary adjuvants and/or diluents and subsequently compressing the mixture in a conventional tabletting machine. Examples of adjuvants or diluents comprise: corn starch, potato starch, talcum, magnesium stearate, gelatine, lactose, gums, and the like. Any other adjuvants or additives usually used for such purposes such as colourings, flavourings, preservatives etc. may be used provided that they are compatible with the active ingredients. Solutions for injections may be prepared by dissolving the active ingredient and possible additives in a part of the solvent for injection, preferably sterile water, adjusting the solution to desired volume, sterilising the solution and filling it in suitable ampules or vials. Any suitable additive conventionally used in the art may be added, such as tonicity agents, preservatives, antioxidants, etc.

Typical examples of recipes for the formulation of the invention are as follows:

1) Tablets containing 5.0 mg of a compound of the invention calculated as the free base:

| Compound | 5.0 mg |
|---|---|
| Lactose | 60 mg |
| Maize starch | 30 mg |
| Hydroxypropylcellulose | 2.4 mg |
| Microcrystalline cellulose | 19.2 mg |
| Croscarmellose Sodium Type A | 2.4 mg |
| Magnesium stearate | 0.84 mg |

2) Tablets containing 0.5 mg of a compound of the invention calculated as the free base:

| Compound | 0.5 mg |
|---|---|
| Lactose | 46.9 mg |
| Maize starch | 23.5 mg |
| Povidone | 1.8 mg |
| Microcrystalline cellulose | 14.4 mg |
| Croscarmellose Sodium Type A | 1.8 mg |
| Magnesium stearate | 0.63 mg |

3) Syrup containing per millilitre:

| Compound | 25 mg |
|---|---|
| Sorbitol | 500 mg |
| Hydroxypropylcellulose | 15 mg |
| Glycerol | 50 mg |
| Methyl-paraben | 1 mg |
| Propyl-paraben | 0.1 mg |
| Ethanol | 0.005 ml |
| Flavour | 0.05 mg |
| Saccharin sodium | 0.5 mg |
| Water | ad 1 ml |

4) Solution for injection containing per millilitre:

| Compound | 0.5 mg |
|---|---|
| Sorbitol | 5.1 mg |
| Acetic Acid | 0.05 mg |
| Saccharin sodium | 0.5 mg |
| Water | ad 1 ml |

What is claimed is:

1. A substituted indole derivative of formula I

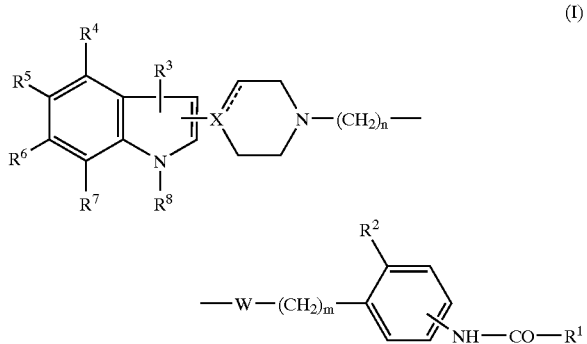

(I)

wherein $R^1$ is hydrogen or $C_{1-6}$-alkyl, $C_{2-6}$-alkenyl, $C_{2-6}$-alkynyl, $C_{3-8}$-cycloalkyl or $C_{3-8}$-cycloalkyl-$C_{1-6}$-alkyl, all of which may be substituted one or more times with substituents selected from halogen, cyano, nitro, amino, hydroxy, thiol, $C_{1-6}$-alkoxy, $C_{1-6}$-alkylthio, trifluoromethyl, trifluoromethylsulfonyl and $C_{1-6}$-alkylsulfonyl, or $R^1$ is aryl, aryl-$C_{1-6}$-alkyl, heteroaryl, heteroaryl-$C_{1-6}$-alkyl where the aryl and heteroaryl groups may be substituted one or more times with substituents selected from halogen, cyano, nitro, amino, $C_{1-6}$-alkyl, $C_{1-6}$-alkoxy, $C_{1-6}$-alkylthio, hydroxy, thiol, trifluoromethyl, trifluoromethylsulfonyl and $C_{1-6}$ alkylsulfonyl, or $R^1$ is —NR'R" wherein R' and R" are independently selected from hydrogen and $C_{1-6}$-alkyl, aryl, aryl-$C_{1-6}$-alkyl, heteroaryl and heteroaryl-$C_{1-6}$-alkyl, all of which may be substituted one or more times with substituents selected from halogen, cyano, nitro, amino, $C_{1-6}$-alkyl, $C_{1-6}$alkoxy, $C_{1-6}$-alkylthio, hydroxy, thiol, trifluoromethyl, trifluoromethylsulfonyl and $C_{1-6}$ alkylsulfonyl, or $R^1$ is a saturated or partially saturated 5- to 6-membered ring containing one, two or three hetero atoms selected from the group consisting of O, S, and N, where N is substituted with $R^9$, wherein $R^9$ is hydrogen or $C_{1-6}$-alkyl optionally substituted with substituents selected from halogen, cyano, nitro, amino, $C_{1-6}$-alkoxy, $C_{1-6}$-alkylthio, hydroxy, thiol, trifluoromethyl, trifluoromethylsulfonyl and $C_{1-6}$ alkylsulfonyl;

W is a bond or an O, S, CO, CS, SO or $SO_2$ group;

n is 0–6, m is 0–6 and n+m is 0–6; provided that when W is O or S, $n \geq 2$, and when W is CO, CS, SO or $SO_2$, $n \geq 1$;

X is C, CH or N and the dotted line emanating from X indicates a bond when X is C and no bond when X is N or CH;

$R^2$ is $C_{1-6}$-alkyl;

$R^3$–$R^7$ are selected from hydrogen, halogen, cyano, nitro, amino, $C_{1-6}$-alkyl, $C_{2-6}$-alkenyl, $C_{2-6}$-alkynyl, $C_{3-8}$-cycloalkyl, $C_{3-8}$-cycloalkyl-$C_{1-6}$-alkyl, $C_{1-6}$-alkoxy, $C_{1-6}$-alkylthio, hydroxy, thiol, trifluoromethyl, trifluoromethylsulfonyl and $C_{1-6}$ alkylsulfonyl;

$R^8$ is hydrogen, $C_{1-6}$-alkyl, $C_{2-6}$-alkenyl, $C_{2-6}$-alkynyl, $C_{3-8}$-cycloalkyl, $C_{3-8}$-cycloalkyl-$C_{1-6}$-alkyl, aryl, aryl-$C_{1-6}$-alkyl, acyl, thioacyl, $C_{1-6}$-alkylsulfonyl, trifluoromethylsulfonyl, or arylsulfonyl or a pharmaceutically acceptable acid addition salt thereof.

2. A compound of claim 1, wherein the indole is bound to X via position 3 of the indole.

3. A compound of claim 1, wherein W is a bond.

4. A compound of claim 3, wherein n+m is 2.

5. A compound of claim 1, wherein $R^2$ is a methyl group.

6. A compound of claim 1, wherein the group —NH—CO—$R^1$ is attached to the phenyl group in the position para to the position of the $R^2$ group.

7. A compound of claim 1, wherein $R^1$ is $C_{1-6}$-alkyl, $C_{3-8}$-cycloalkyl, $C_{3-8}$-cycloalkyl-$C_{1-6}$-alkyl, phenyl, phenyl-$C_{1-6}$-alkyl, furanyl, thienyl, pyridyl, pyrrolyl, pyrimidyl, wherein the phenyl groups may be substituted one or more times with substituents selected from halogen, cyano, nitro, amino, $C_{1-6}$-alkyl, $C_{1-6}$-alkoxy, $C_{1-6}$-alkylthio, hydroxy, trifluoromethyl, trifluoromethylsulfonyl and $C_{1-6}$-alkylsulfonyl, or $R^1$ is —NR'R" wherein one of R' and R" is hydrogen and the other of R' and R" is selected from $C_{1-6}$-alkyl, phenyl and phenyl-$C_{1-6}$-alkyl, wherein the phenyl groups may be substituted one or more times with substituents selected from halogen, cyano, nitro, amino, $C_{1-6}$-alkyl, $C_{1-6}$-alkoxy, $C_{1-6}$-alkylthio, hydroxy, trifluoromethyl, trifluoromethylsulfonyl and $C_{1-6}$-alkylsulfonyl, or $R^1$ is a tetrahydropyranyl or a morpholino, thiomorpholino, piperidino, piperazino or a N-(hydroxy-$C_{1-6}$-alkyl)piperazinyl group.

8. A compound of claim 1 selected from
3-(1-{2-[5-(Acetylamino)-2-methylphenyl]ethyl}piperidin-4-yl)-6-chloro-1H-indole;
3-(1-{2-[5-(Cyclobutylmethanoylamino)-2-methylphenyl]ethyl}piperidin-4-yl)-5-fluoro-1H-indole;
3-(1-{2-[5-(Acetylamino)-2-methylphenyl]ethyl}piperidin-4-yl)-5-fluoro-1H-indole;
3-(1-{2-[2-Methyl-5-(thiophen-2-ylmethanoylamino)phenyl]ethyl}piperidin-4-yl)-5-chloro-1H-indole;
3-(1-{2-[2-Methyl-5-(3-methoxybenzoylamino)phenyl]ethyl}piperidin-4-yl)-5-chloro-1H-indole;
3-(1-{2-[5-(Cyclopropylmethanoylamino)-2-methylphenyl]ethyl}piperidin-4-yl)-5-fluoro-1H-indole;
3-(1-{2-[2-Methyl-5-(thiophen-2-ylmethanoylamino)phenyl]ethyl}piperidin-4-yl)-5fluoro-1H-indole;
3-(1-{2-[5-(Isobutanoylamino)-2-methylphenyl]ethyl}piperidin-4-yl)-5-fluoro-1H-indole;
3-(1-{2-[2-Methyl-5-(pivaloylamino)phenyl]ethyl}piperidin-4-yl)-5-fluoro-1H-indole;
3-(1-{2-[5-(Hexanoylamino)-2-methylphenyl]ethyl}piperidin-4-yl)-5-fluoro-1H-indole;
3-(1-{2-[5-(4-Fluorobenzoylamino)-2-methylphenyl]ethyl}piperidin-4-yl)-5-fluoro-1H-indole;
3-(1-{2-[5-(3-Methoxybenzoylamino)-2-methylphenyl]ethyl}piperidin-4-yl)-5-fluoro-1H-indole;
3-(1-{2-[2-Methyl-5-(pyridin-3-ylmethanoylamino)phenyl]ethyl}piperidin-4-yl)-5-fluoro-1H-indole;
3-(1-{2-[2-Methyl-5-(3-phenylpropanoylamino)phenyl]ethyl}piperidin-4-yl)-5-fluoro-1H-indole;
3-(1-{2-[2-Methyl-5-(4-methylbenzoylamino)phenyl]ethyl}piperidin-4-yl)-5-fluoro-1H-indole;
3-(1-{2-[2-Methyl-5-(3-Methyl-3-phenylureido)phenyl]ethyl}piperidin-4-yl)-6-chloro-1H-indole;
3-(1-{2-[5-(Cyclopropylmethanoylamino)-2-methylphenyl]ethyl}piperidin-4-yl)-6-chloro-1H-indole;
3-(1-{2-[2-Methyl-5-(thiophen-2-ylmethanoylamino)phenyl]ethyl}piperidin-4-yl)-6-chloro-1H-indole;
3-(1-{2-[5-(Isobutanoylamino)-2-methylphenyl]ethyl}piperidin-4-yl)-6-chloro-1H-indole;
3-(1-{2-[5-(3-Methoxybenzoylamino)-2-methylphenyl]ethyl}piperidin-4-yl)-6-chloro-1H-indole;
3-(1-{2-[2-Methyl-5-(pyridin-3-ylmethanoylamino)phenyl]ethyl}piperidin-4-yl)-6-chloro-1H-indole;
3-[1-(2-{5-[2-(4-Methoxyphenyl)ethanoylamino]-2-methylphenyl}ethyl)piperidin-4-yl]-6-chloro-1H-indole;
3-(1-{2-[2-Methyl-5-(4-methylbenzoylamino)phenyl]ethyl}piperidin-4-yl)-6-chloro-1H-indole;
3-[1-(2-{5-[(Cyclopentylmethanoyl)amino]-2-methylphenyl}ethyl)piperidin-4-yl]-6-chloro-1H-indole;
3-(1-{2-[2-Methyl-5-(morfolin-4-ylmethanoylamino)phenyl]ethyl}piperidin-4-yl)-5-fluoro-1H-indole;
3-[1-(2-{5-[3-(4-Fluorophenyl)ureido]-2-methylphenyl}ethyl)piperidin-4-yl]-5-fluoro-1H-indole;
3-(1-{2-[5-(Hexanoylamino)-2-methylphenyl]ethyl}piperidin-4-yl)-7-chloro-1H-indole;
3-(1-{2-[2-Methyl-5-(tetrahydropyran-4-ylmethanoylamino)phenyl]ethyl}piperidin-4-yl)-5-fluoro-1H-indole;
3-(1-{2-[5-(4-Chlorobenzoylamino)-2-methylphenyl]ethyl}piperidin-4-yl)-7-chloro-1H-indole;
3-(1-{2-[5-(3-Cyclohexylpropanoylamino)-2-methylphenyl]ethyl}piperidin-4-yl)-5-fluoro-1H-indole;
3-[1-(2-{5-[(3-Phenylpropanoyl)amino]-2-methylphenyl}ethyl)piperidin-4-yl]-7-chloro-1H-indole;
3-[1-(2-{5-[(2-Phenylethanoyl)amino]-2-methylphenyl}ethyl)piperidin-4-yl]-7-chloro-1H-indole;
3-(1-{2-[2-Methyl-5-(4-methylbenzoylamino)phenyl]ethyl}piperidin-4-yl)-7-chloro-1H-indole;
3-(1-{2-[5-(Cyclopropylmethanoylamino)-2-methylphenyl]ethyl}piperidin-4-yl)-7-chloro-1H-indole;
3-[1-(2-{5-[2-(4-Fluorophenyl)ethanoylamino]-2-methylphenyl}ethyl)piperidin-4-yl]-7-chloro-1H-indole;
3-[1-(2-{5-[2-(4-Methoxyphenyl)ethanoylamino]-2-methylphenyl}ethyl)piperidin-4-yl]-7-chloro-1H-indole;
3-[1-(2-{5-[(Cyclobutylmethanoyl)amino]-2-methylphenyl}ethyl)piperidin-4-yl]-7-chloro-1H-indole;
3-(1-{2-[5-(benzoylamino)-2-Methylphenyl]ethyl}piperidin-4-yl)-7-chloro-1H-indole;
3-(1-{2-[5-(4-Fluorobenzoylamino)-2-methylphenyl]ethyl}piperidin-4-yl)-7-chloro-1H-indole;
3-(1-{2-[5-(4-Methoxybenzoylamino)-2-methylphenyl]ethyl}piperidin-4-yl)-7-chloro-1H-indole;
3-[1-(2-{2-Methyl-5-[(pyridin-3-ylmethanoyl)amino]phenyl}ethyl)piperidin-4-yl]-7-chloro-1H-indole;
3-[1-(2-{2-Methyl-5-[(pyridin-4-ylmethanoyl)amino]phenyl}ethyl)piperidin-4-yl]-7-chloro-1H-indole;
3-[1-(2-{2-Methyl-5-[(thiophen-2-ylmethanoyl)amino]phenyl}ethyl)piperidin-4-yl]-7-chloro-1H-indole;
3-[1-(2-{2-Methyl-5-[(thiophen-3-ylmethanoyl)amino]phenyl}ethyl)piperidin-4-yl]-7-chloro-1H-indole;
3-[1-(2-{2-Methyl-5-[(1-[1,2,3]thiadiazol-5-ylmethanoyl)amino]phenyl}ethyl)-piperidin-4-yl]-7-chloro-1H-indole;
3-{1-[2-(5-Acetylamino-2-methylphenyl)-ethyl]-3,6-dihydro-2H-pyridin-4-yl}-5-fluoro-1H-indole;
3-[1-(2-{2-Methyl-5-[(pyridin-3-ylmethanoyl)-amino]-phenyl}-ethyl)-3,6-dihydro-2H-pyridin-4-yl]-5-fluoro-1H-indole;
3-[1-(2-{5-[(4-Fluorophenylmethanoyl)-amino]-2-methylphenyl}-ethyl)-3,6-dihydro-2H-pyridin-4-yl]-5-fluoro-1H-indole;
3-{1-[2-(5-Acetylamino-2-methylphenyl)-ethyl]-3,6-dihydro-2H-pyridin-4-yl}-7-chloro-1H-indole;
3-[1-(2-{2-Methyl-5-[(pyridin-3-ylmethanoyl)-amino]-phenyl}-ethyl)-3,6-dihydro-2H-pyridin-4-yl]-7-chloro-1H-indole and
3-[1-(2-{5-[(4-Fluorophenylmethanoyl)-amino]-2-methylphenyl}-ethyl)-3,6-dihydro-2H-pyridin-4-yl]-7-chloro-1H-indole or a pharmaceutically acceptable salt thereof.

9. A pharmaceutical composition comprising a compound of claim 1 in a therapeutically effective amount together with one or more pharmaceutically acceptable carriers or diluents.

10. A method of treating the positive and negative symptoms of schizophrenia, other psychoses, anxiety disorders, depression, aggression, side effects induced by conventional antipsychotic agents, migraine, cognitive disorders, ADHD and in the improvement of sleep comprising administration of a therapeutically acceptable amount of a compound of claim 1 to a patient in need thereof.

11. The method of claim 10, wherein said anxiety disorders are selected from the groups consisting of generalised anxiety disorder, panic disorder and obsessive compulsive disorder.

* * * * *